(12) United States Patent
Kim et al.

(10) Patent No.: US 6,261,225 B1
(45) Date of Patent: Jul. 17, 2001

(54) APPARATUS FOR GENERATING FAR INFRARED RAYS AND DISPLAY SYSTEM ADOPTING THE SAME

(75) Inventors: Hun-soo Kim, Seoul; Eun-keu Oh, Suwon; Sang-wook Wu; Jeong-hee Kim, both of Sungnam; Jina Namgoong; Kyoung-mi Cho, both of Suwon, all of (KR)

(73) Assignee: Samsung Display Devices Co., Ltd., Kyungki-Do (KR)

( * ) Notice: Subject to any disclaimer, the term of this patent is extended or adjusted under 35 U.S.C. 154(b) by 0 days.

(21) Appl. No.: 09/296,535

(22) Filed: Apr. 22, 1999

(30) Foreign Application Priority Data

| May 7, 1998 | (KR) | 98-16295 |
| May 18, 1998 | (KR) | 98-8198 |
| Jul. 3, 1998 | (KR) | 98-26834 |
| Jul. 3, 1998 | (KR) | 98-26835 |
| Nov. 24, 1998 | (KR) | 98-50475 |

(51) Int. Cl.$^7$ ................................................ A61M 21/00
(52) U.S. Cl. ................................................................ 600/27
(58) Field of Search .................... 600/27, 26; 313/477 R; 348/553; 350/353

(56) References Cited

U.S. PATENT DOCUMENTS

| 4,687,967 | * | 8/1987 | Rusche et al. | 313/477 R |
| 5,016,990 | * | 5/1991 | Dobson | 350/353 |
| 5,719,635 | * | 2/1998 | Han | 348/553 |

* cited by examiner

Primary Examiner—John P. Lacyk
Assistant Examiner—Brian Szmal
(74) Attorney, Agent, or Firm—Leydig, Voit & Mayer, Ltd.

(57) ABSTRACT

A display device including a main body case having an aperture in a front side, a cathode ray tube in the main body case, a far infrared radiating material on at least one side surface inside the main body case, and a modulator for modulating far infrared rays radiated from the far infrared radiating material and emitted through the aperture.

20 Claims, 10 Drawing Sheets

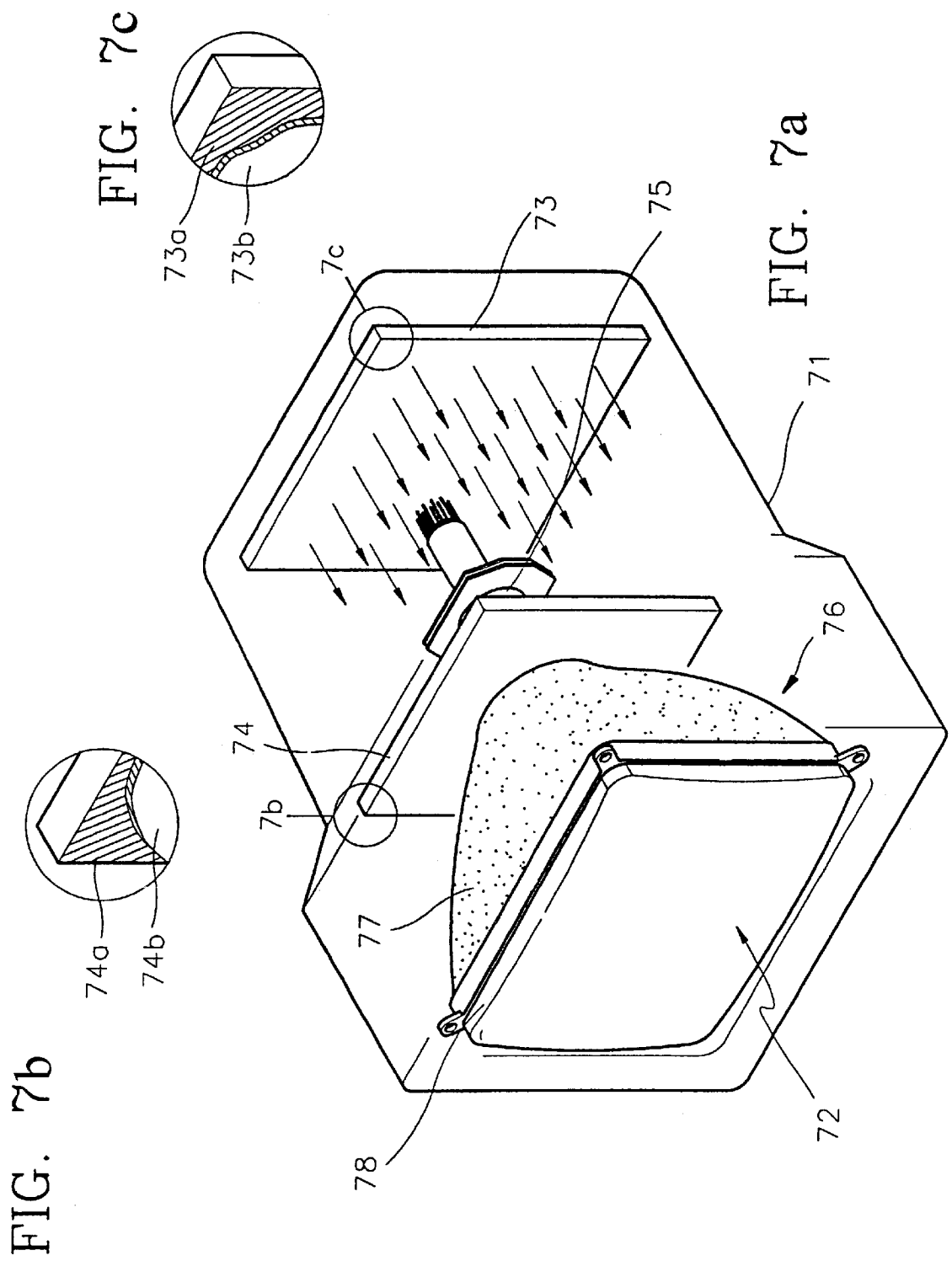

APPARATUS FOR GENERATING FAR INFRARED RAYS AND DISPLAY SYSTEM ADOPTING THE SAME

BACKGROUND OF THE INVENTION

1. Field of the Invention

The present invention relates to an apparatus for generating far infrared rays which are good for a living body and a display system adopting the same.

2. Description of the Related Art

Far infrared rays are a type of light like visible rays. A wavelength used as a variable for discriminating the far infrared rays is longer than that of the visible rays. Far infrared rays have a wavelength of about 5.6 to 1000 $\mu$m. From the standpoint of a photon being the basic unit of light, the energy of a far infrared ray photon is lower than that of a visible ray photon. The far infrared rays can control absorption, reflection, and transmission if using a specific material, and are applied to a far infrared ray camera since, although some are absorbed in the air, they are sufficiently transmitted by a predetermined amount or more.

Such far infrared rays accelerate the growth of a plant, and ripen food. In addition, it is known that the far infrared rays have the following various advantages: a biological effect, agitation of water molecules, maintaining of the freshness of food, and sterilization. A Qi (subtle energy) master emits a particular frequency, e.g., far infrared rays modulated to about 1 Hz. It is known that these far infrared rays have remedial values such as promotion of physical health and alleviation of pain. The frequency of these far infrared rays is modulated according to the degree of stability or instability in breathing.

In particular, applications of far infrared rays beneficial to human bodies have been studied in connection with harmful electromagnetic waves generated from various electronic equipment.

For example, electromagnetic waves, generated from display devices such as a computer monitor and a cathode ray tube, which use emission of electron beams, contribute to a malfunction of neighboring precision electronic equipment, and are biologically hazardous to human bodies. It is known that such harmful electromagnetic waves are associated with skin roughness, miscarriage, sterility, and the production of cancer. Display devices emit large numbers of positive ions but generate no negative ions. Thus, a special negative charge generating apparatus is required to prevent the bad influence on human bodies due to the imbalance of charge.

Also, electronic components operating at high temperature cause an unpleasant smell or lower the humidity of the room. Such environments can make a user quickly feel languid or fatigued.

A far infrared radiating material is adopted to improve the biological state of the user by enhancing the using environment of such electronic equipment and accelerating the biological relaxation of a user.

A cathode ray tube (CRT) adopting the far infrared radiating material referred to as a "bio CRT" is used in a bio TV, a bio computer monitor, etc. The bio CRT has a coating of a far infrared radiating material on an inner surface or outer surface of a panel of the CRT. Hence, when the temperature of the panel increases with the operation of the CRT, the far infrared rays are emitted.

Far infrared radiating materials include silicon dioxide, aluminum oxide, magnesium oxide, cobalt oxide, titanium oxide, calcium oxide, sodium oxide, and other transition metal oxides. Also, the far infrared radiating material is white or a color close to white in order to maintain the radiation efficiency of a luminescent material, and a pure material, not mixed with steel, cobalt, or nickel, each degrading the luminescence of a luminescent material, is used.

However, upon operation of the CRT, only some of the far infrared rays are emitted via the front surface of the CRT, and the residuals are emitted to the rear of the CRT. Accordingly, a small influence is exerted on a user in front of the CRT.

Therefore, a system capable of emitting many far infrared rays to the front side of a display is required to have a good influence on the biological state of a user in front of the display.

SUMMARY OF THE INVENTION

To solve the above problem, it is an objective of the present invention to provide a far infrared ray generating apparatus capable of emitting many far infrared rays profitable to human bodies in one direction, and a display device adopting the same.

Accordingly, to achieve the above objective, there is provided a far infrared ray generating apparatus comprising: a case having an aperture formed in the front side thereof; a far infrared radiating material formed on the inside surface of the case, for radiating far infrared rays; and a modulating means installed in the case for modulating the far infrared rays radiated from the far infrared radiating material at a predetermined modulation frequency.

The modulating means is comprised of at least two modulating means each including a driving unit and a fan rotated by the driving unit, the fans driven at different revolutions to modulate the far infrared rays at a frequency of 0 to 10 Hz.

According to another embodiment of the present invention, the modulating means comprises: a hinged member rotatably installed inside a passage in the case for opening or closing the passage; and a driving unit for rotating the hinged member.

According to an aspect of the present invention, there is provided a display device comprising: a main body case having an aperture formed in the front side thereof; a cathode ray tube installed in the main body case; a far infrared radiating material formed on at least one side surface inside the main body case; and a modulating means for modulating far infrared rays, radiated from the far infrared radiating material and emitted through the aperture, at a predetermined frequency.

According to another aspect of the present invention, there is provided a display device comprising: a main body case having a first aperture formed in the front side thereof; a cathode ray tube installed in the main body case; and a far infrared ray generator including a case having a second aperture formed on the front surface thereof, aligned with the first aperture, a far infrared radiating material formed on the inside surface of the main body case for radiating far infrared rays, and a modulating means installed in the main body case for modulating far infrared rays radiated from the far infrared radiating material at a predetermined frequency.

In this specification, there is provided a display device comprising: a main body case; a cathode ray tube installed inside the main body case; and a far infrared radiating material coated on at least one side surface inside the main body case and formed largely of a material selected from the group consisting of aluminum oxide and silicon oxide.

Also, there is provided a display device comprising: a main body case; a cathode ray tube installed inside the main body case; and at least one far infrared ray emission plate installed inside the main body case, the far infrared ray emission plate comprised of a plate and a far infrared radiating material coated on the plate.

Furthermore, there is provided a display device comprising: a main body case; a cathode ray tube installed inside the main body case; a far infrared radiating material formed on at least one side surface inside the main body case; and at least one reflection plate installed in the main body case for reflecting far infrared rays radiated from the far infrared radiating material.

BRIEF DESCRIPTION OF THE DRAWINGS

The above objective and advantage of the present invention will become more apparent by describing in detail preferred embodiments thereof with reference to the attached drawings in which:

FIGS. 7a, 7b, and 7c are a partial incision perspective view illustrating a display device according to a fifth embodiment of the present invention and two detail views of part of the device of FIG. 7a, respectively;

DESCRIPTION OF THE PREFERRED EMBODIMENTS

Figure 1:
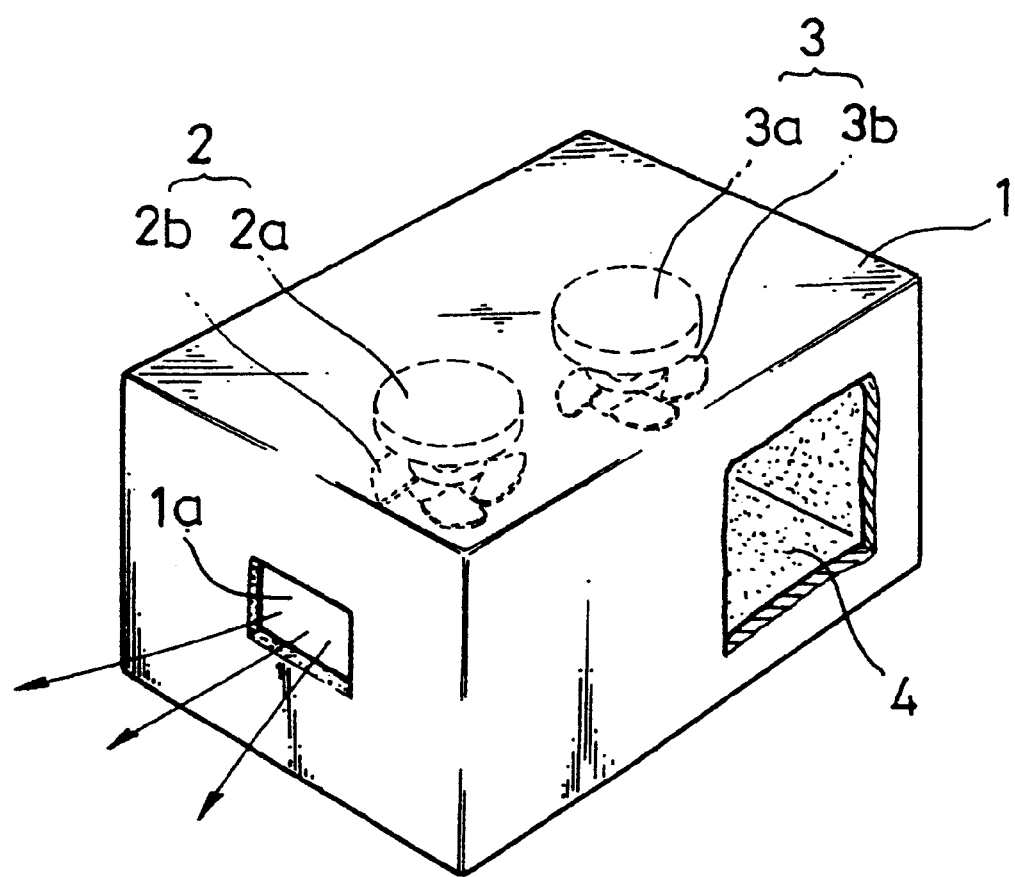
FIG. 1 is a partially cut away perspective view illustrating a far infrared ray generating apparatus according to a first embodiment of the present invention.

Referring to FIG. 1, a far infrared ray generating device according to a first embodiment of the present invention includes a case 1 having an aperture 1a formed on its front surface, and at least one modulator (here, two modulators 2 and 3) installed within the case 1.

A far infrared radiating material 4 for radiating far infrared rays coats the inner surfaces of the case 1. It is well-known that the far infrared radiating material 4 is at least one material selected from the group consisting of silicon dioxide ($SiO_2$), aluminum oxide ($Al_2O_3$), zirconium oxide, magnesium oxide (MgO), calcium oxide (CaO), titanium oxide ($TiO_2$), sodium oxide, phosphorus oxide, potassium oxide ($K_2O$), cobalt oxide, and other transition metal oxides.

The far infrared radiating material 4 can be formed by applying a loess, a type of far infrared radiating material, for radiating far infrared rays. Loess consists largely of silicon dioxide ($SiO_2$) and aluminum oxide ($Al_2O_3$). Ferrous oxide ($Fe_2O_2$), calcium oxide (CaO), potassium oxide ($K_2O$), magnesium oxide (MgO), and titanium oxide ($TiO_2$) are added to form the loess.

Meanwhile, various far infrared radiating materials including the loess can coat the outside surfaces of a far infrared ray generating apparatus and a display system to be described later.

Hereinbelow, the far infrared radiating material used in this specification and claims is to be understood as the above-described material.

The modulators 2 and 3 modulate the frequency of far infrared rays, emitted from the far infrared radiating material 4, at a frequency of 0 to 10 Hz which is suitable for human bodies. The modulators 2 and 3 respectively include driving units 2a and 3a and fans 2b and 3b which are rotated respectively by the driving units 2a and 3a.

It is preferable that at least two modulators 2 and 3 be used. Here, the frequencies of modulation of the fans 2b and 3b are different. That is, the far infrared rays are modulated by the first fan 2b within a frequency range of 0 Hz to 2 Hz, and are also modulated by the second fan 3b within a frequency range of 0 to 10 Hz. Preferably, the first fan 2b is driven at a frequency of 0.3 Hz by the first driving unit 2a, thus allowing the modulation of far infrared rays at a frequency of 0.3 Hz. Also, the second fan 3b is driven at a frequency of 1 Hz by the second driving unit 3a, thus allowing the modulation of far infrared rays at a frequency of 1 Hz.

Figure 11:
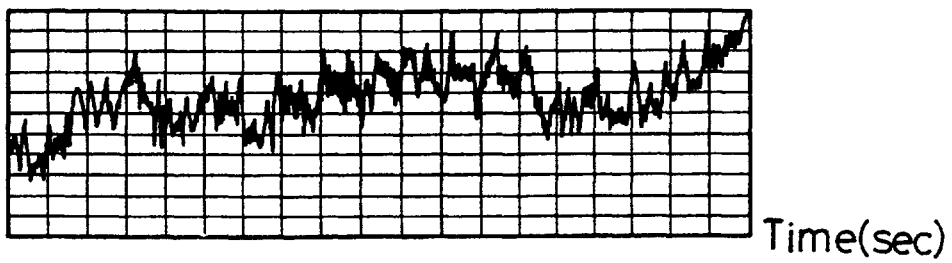
FIG. 11 shows the waveform of a far infrared signal measured from the hand of an ordinary person.
Figure 12:
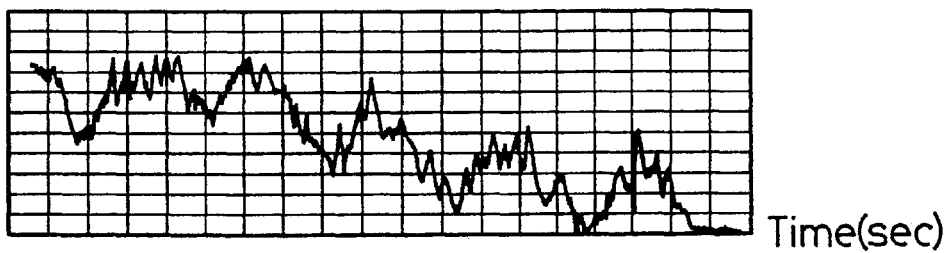
FIG. 12 shows the waveform of a far infrared signal measured from the hand of an ordinary person upon relaxed breathing.

FIG. 11 is a graph showing a signal emitted from the hand of an unrelaxed person, in which the radiant intensity of a far infrared ray changes unstably. However, FIG. 12, comparable with FIG. 11, is a graph showing a signal emitted from the hand of the same person as in FIG. 11. As can be seen from FIG. 12, The radiation intensity of a far infrared ray changes at a frequency of 0.22 to 0.3 Hz. A frequency between 0.2 Hz and 0.3 Hz corresponds to the breathing frequency of the body of a relaxed person, and the frequency of a far infrared ray emitted from a person's hand when his or her body relaxes is shown in FIG. 12.

Figure 13:
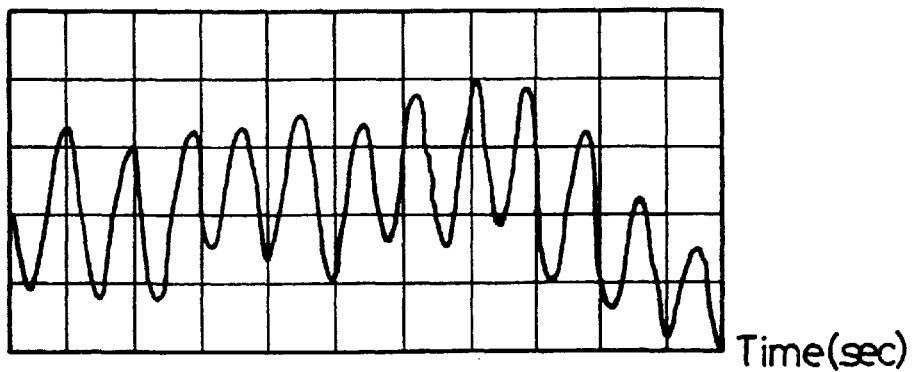
FIG. 13 shows the waveform of a far infrared signal measured from the hand of a Qi (subtle energy) master.

FIG. 13 shows a far infrared ray waveform having a frequency of 1 Hz generated from the hand of a Qi master. As can be seen in FIG. 13, the radiation intensity of a far infrared ray changes at a frequency of 1 Hz. The far infrared ray with a frequency of 1 Hz is known to be beneficial for a human body by stabilizing brain waves and heartbeat due to reinforcement of parasympathetic nerves.

In the graphs of FIGS. 11 through 13, the X-axis denotes time in one second increments, and the Y-axis denotes the radiation intensity of a far infrared ray. Here, the radiation intensity of a far infrared ray can be calculated from the mutual relative values among three indices. In the three different cases of experiments, an identical measurer was used. The measurer, a sensor using a semiconductor, is a thermal sensor which reacts to far infrared rays of 6 to 14 $\mu$m wavelength. The relative values as shown in FIGS. 11 through 13 are obtained by outputting far infrared radiation intensity data from the measurer in relation to time, as graphs.

A stepping motor, a solenoid, or a driving device using an electromagnet can be adopted as the driving units 2a and 3a, and the driving units 2a and 3a are controlled by a controller (not shown).

The far infrared radiating material 4 can coat not only on the inside of the case 1 but also on the fans 2b and 3b. Also, the number of modulators can be appropriately chosen without being limited to the present embodiment.

According to the first embodiment, far infrared rays generated by the far infrared radiating material 4 inside the case 1 are appropriately frequency-modulated by the modulators 2 and 3 and radiated in one direction through the aperture 1a.

Figure 2:
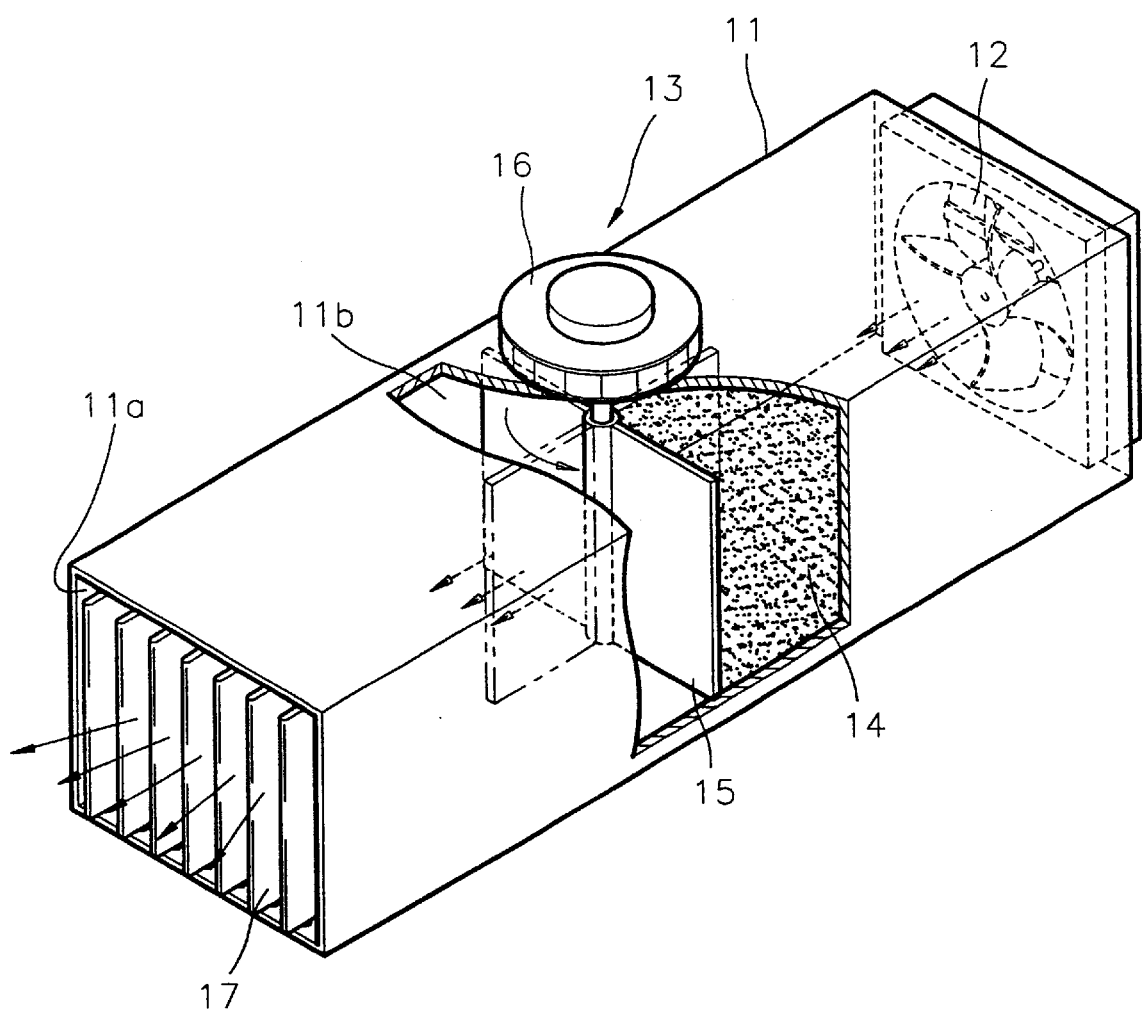
FIG. 2 is a partially cut away perspective view illustrating a far infrared ray generating apparatus according to a second embodiment of the present invention.

FIG. 2 illustrates a far infrared ray generating apparatus according to a second embodiment of the present invention.

As shown in FIG. 2, the far infrared ray generating apparatus includes a case 11 having an aperture 11a formed on the front side, an emission fan 12 installed inside, and a modulator 13 for modulating far infrared rays.

A far infrared radiating material 14 for radiating far infrared rays is coated on the inner surface of the case 11. The emission fan 12 is installed on the rear side of the case 11, and forcibly emits far infrared rays, generated by the far infrared radiating material 14, through the aperture 11a.

The modulator 13 modulates the radiated quantity of far infrared rays generated within the case 11 at a specific frequency, is rotatably installed in a passage 11b of the case 11, and is comprised of a hinged member 15 for opening or closing the passage 11b, and a stepping motor 16 for rotating the hinged member 15. The hinged member 15 is comprised of four blades equally spaced at angular intervals to allow continuous opening and closing. The stepping motor 16 is controlled by a controller (not shown) and thus rotates 0.5 Hz so that the hinged member 15 can open and close one time per one second. Therefore, the radiation frequencies of far infrared ray are regulated to 1 Hz.

The amplitude modulation denotes changing of the intensity at which a far infrared ray is radiated from a far infrared radiating material. The above-mentioned frequency denotes not the frequency of a photon, being a basic unit of light, but a cycle relating to how fast the hinged member 15 should rotate to adjust the radiated quantity of specific light being far infrared rays.

Alternatively, the stepping motor 16 can be replaced by a solenoid.

Also, it is preferable that a grille 17 is installed in the aperture 11a so as to control the emission quantity of far infrared rays.

In the far infrared ray generating apparatus having such a configuration, far infrared rays generated in the case 11 are emitted toward the front aperture 11a by the emission fan 12 while being appropriately modulated by the modulator 13.

According to the present invention, the far infrared ray generating apparatus shown in FIGS. 1 and 2 are applied to a display device.

Figure 3:
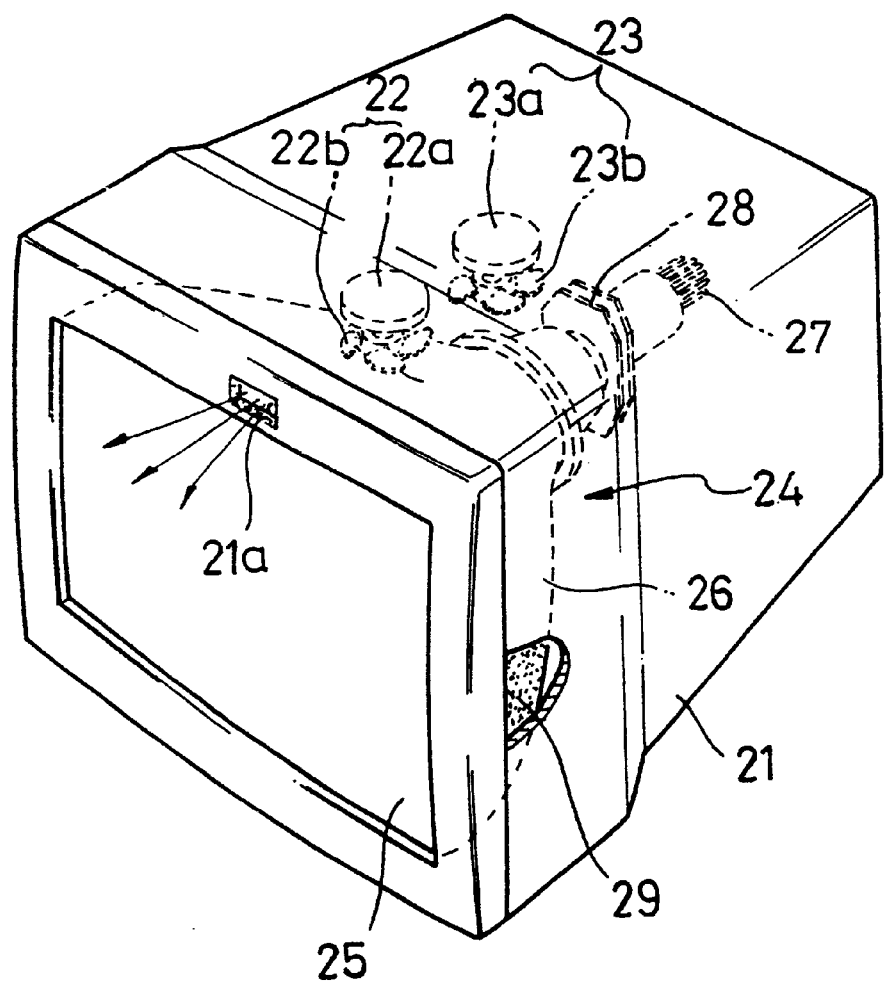
FIG. 3 is a partially cut away perspective view illustrating a display device including a far infrared ray generating apparatus, according to a first embodiment of the present invention.

FIG. 3 illustrates a display device adopting a far infrared ray generating apparatus, according to a first embodiment of the present invention. Referring to FIG. 3, the display device includes a cathode ray tube (CRT) 24 installed in a main body case 21, and modulators 22 and 23 installed within the main body case 21 for modulating the radiation frequencies of generated far infrared rays.

The CRT 24 includes a panel 25 onto which a fluorescent film is coated, and a funnel 26, sealed with the panel 25, onto which an electron gun 27 and a deflection yoke 28 are installed. A far infrared radiating material 29 coats onto a predetermined portion inside the main body case 21, preferably, on the outer surface of the funnel 26 of the CRT 24.

It is preferable that two modulators 22 and 23 are provided. The modulators 22 and 23 are respectively comprised of driving units 22a and 23a and fans 22b and 23b which are rotated by the driving units 22a and 23a. The first modulator 22 modulates the radiation frequencies of far infrared rays at a frequency of 0 to 2 Hz, and the second modulator 23 modulates the frequency of far infrared rays at a frequency of 0 to 10 Hz. Preferably, the first fan 22b is driven at a frequency of 0.15 Hz by the first driving unit 22a allowing modulation of far infrared rays at 0.3 Hz, and the second fan 23b is driven at a frequency of 0.5 Hz by the second driving unit 23a allowing modulation of far infrared rays at 1 Hz.

A stepping motor, a solenoid, or a driving device using an electromagnet can be used as the driving units 22a and 23a, and the driving units 22a and 23a are controlled by a controller (not shown).

According to the present embodiment, far infrared rays, radiated from the far infrared radiating material 29 on the outer surface of the funnel 26 of the CRT 24, are appropriately modulated by the modulators 22 and 23, and emitted toward the front of the display device via an aperture 21a formed in the front surface of the main body case 21.

Figure 4:
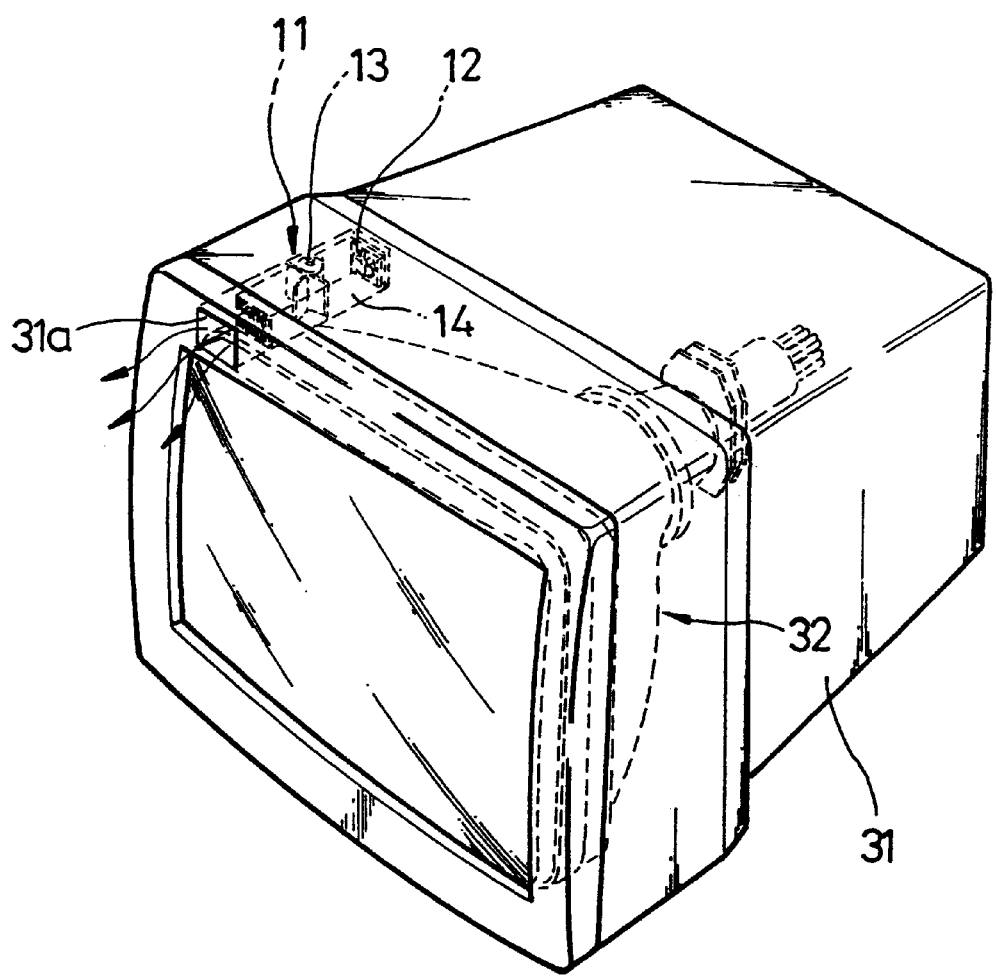
FIG. 4 is a partially cut away perspective view illustrating a display device according to a second embodiment of the present invention.

FIG. 4 illustrates a display device including a far infrared ray generating apparatus, according to a second embodiment of the present invention.

The display device of the present embodiment in FIG. 4 adopts the far infrared ray generating apparatus of FIG. 2. In FIG. 4, the same reference numerals as those of FIG. 2 denote the same members.

As shown in FIG. 4, the far infrared ray generating apparatus is installed inside a main body case 31 in which a CRT 32 is installed, and far infrared rays are emitted toward the front of the display device via an aperture 31 a formed in the front surface of the main body case 31. Preferably, the far infrared ray generating apparatus is electrically connected to the display device so as to operate at the same time as the display device. The far infrared ray generating apparatus may also be installed on the outside of the main body case 31 of the display, however this will not be described.

Figure 5:
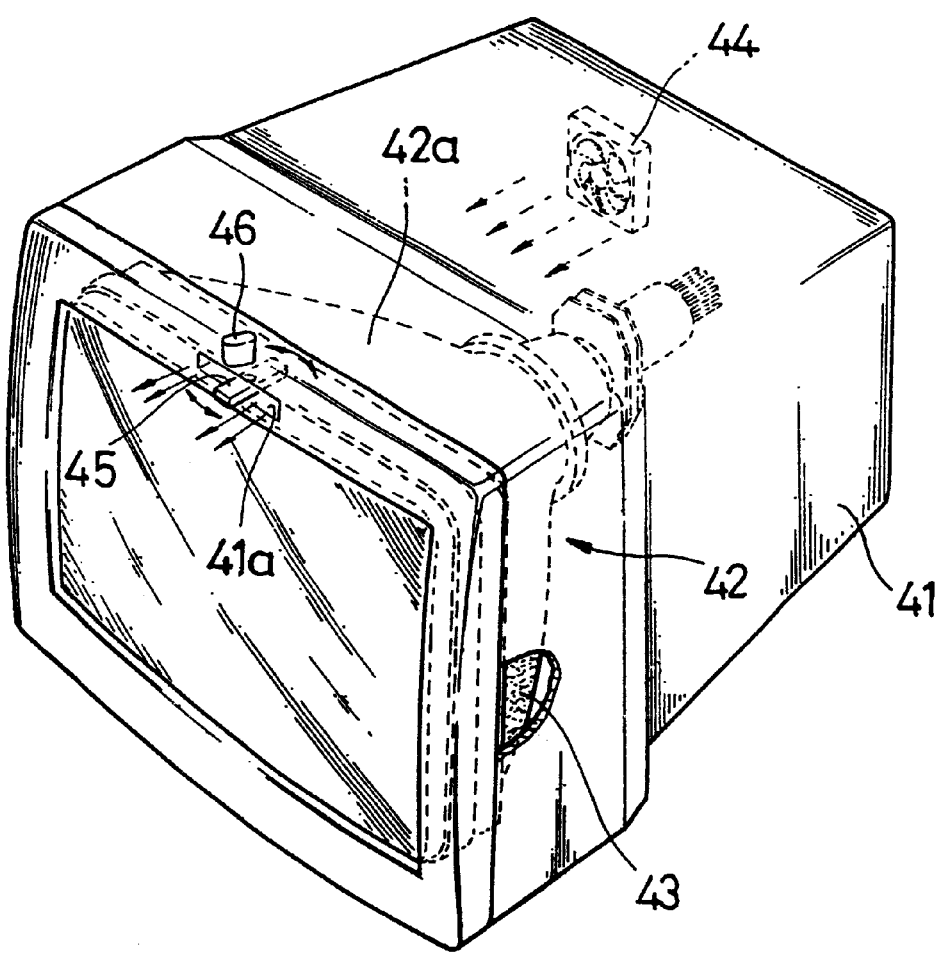
FIG. 5 is a partially cut away perspective view illustrating a display device according to a third embodiment of the present invention.

FIG. 5 illustrates a display device including the far infrared ray generating apparatus, according to a third embodiment of the present invention.

As shown in FIG. 5, a CRT 42 is installed inside a main body case 41 of a display device, and a far infrared radiating material 43 is coated on the outer surface of a funnel 42a of the CRT 42.

An aperture 41a is formed in the front surface of the main body case 41, and a hinged member 45 is rotatably installed on the aperture 41a and opens or closes the aperture 41a according to the driving of a driving unit 46. A stepping motor, a solenoid, or the like can be adopted as the driving unit 46, and the driving unit rotates the hinged member 45 at a predetermined number of rotations under the control of an unshown controller.

An emission fan 44 is installed inside the main body case 41, for emitting far infrared rays, radiated from the far infrared radiating material 43, toward the front of the display device via the front aperture 41 a of the main body case 41.

When power is applied to the display device according to the present embodiment and the display device is thus driven, the aperture 41a continuously opens and closes while the hinged member 45 is rotated by the driving unit 46a predetermined rotational speed. When the aperture 45 is opened, the far infrared rays radiated from the far infrared radiating material 43 coated on the surface of the funnel 42a of the CRT 42 are forcibly emitted toward the front of the display device by the action of the emission fan 44. The radiation intensity of the far infrared rays emitted toward the front of the display device through the aperture 41a is changed according to the rotation of the hinged member 45.

In particular, with an increase in the temperature of the CRT 42, more far infrared rays are radiated from the far infrared radiating material 43. Also, these far infrared rays assume the form of thermal waves other than electromagnetic waves, and the thermal waves are emitted toward the front of the display device by the emission fan 44. By reference, far infrared rays are types of thermal waves.

Alternatively, far infrared rays can be emitted by the continuous rotation of the hinged member 45 without installing the emission fan 44.

Figure 6A:
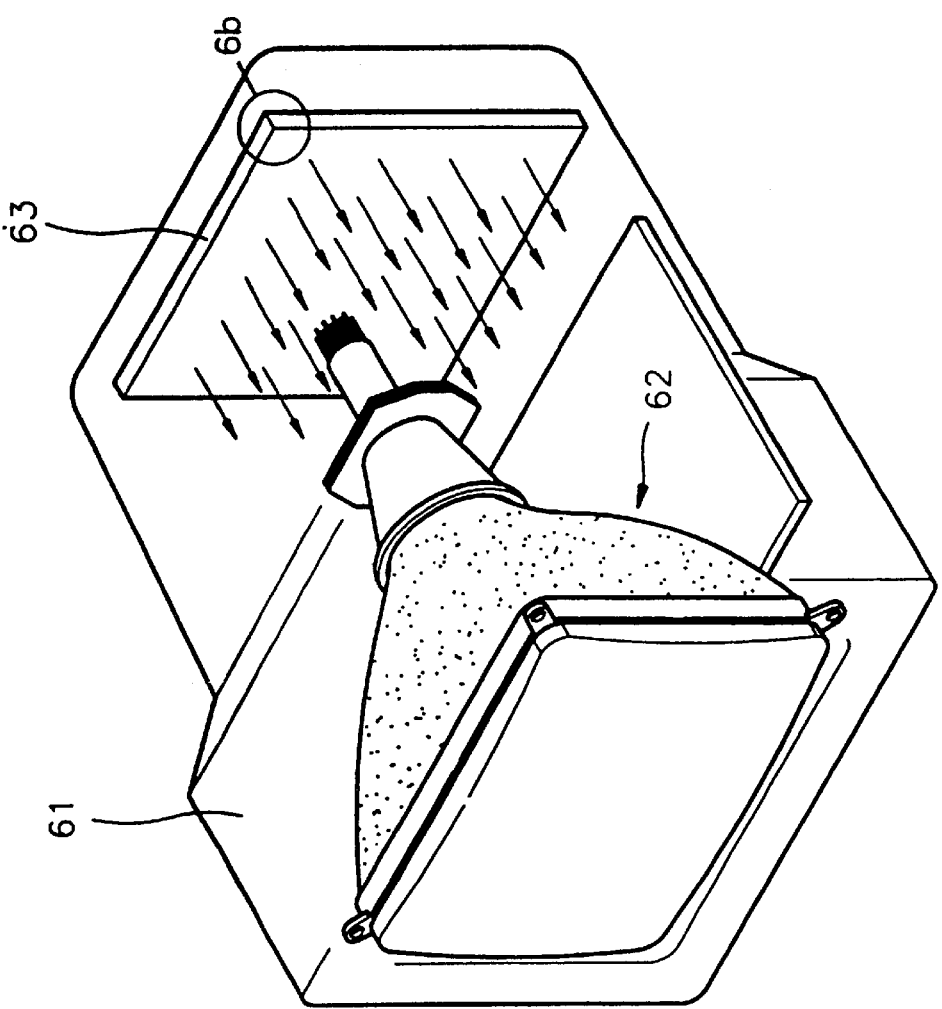
FIGS. 6a and 6b are a partially cut away perspective view illustrating a display device according to a fourth embodiment of the present invention and a detail view of part of the device of FIG. 6a, respectively.
Figure 6B:
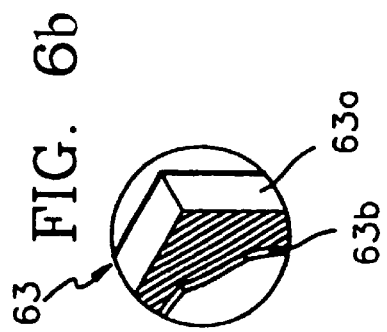

FIGS. 6a and 6b illustrate a display device according to a fourth embodiment of the present invention. As shown in FIG. 6b, a CRT 62 is installed in a main body case 61, and a far infrared radiating plate 63 is installed to the rear of the CRT 62.

The far infrared radiating plate 63 is manufactured by applying a far infrared radiating material 63b to the surface of a plate 63a having a predetermined thickness and area.

According to the present embodiment, since the far infrared radiating plate 63 is installed to the rear of the CRT 62, the far infrared rays radiated from the far infrared radiating plate 63 can be emitted toward the front of the CRT 62.

FIGS. 7a, 7b, and 7c illustrate a display device according to a fifth embodiment of the present invention. Referring to FIG. 7a, the display device includes a CRT 72 housed inside a main body case 71, a main-reflection plate 73 installed to the rear of the CRT 72, and a sub-reflection plate 74 interposed between a funnel 76 and a deflection yoke 75 of the CRT 72.

An armored graphite 77 coats the outer circumferential surface of the funnel 76 of the CRT 72, and a far infrared radiating material is evenly mixed in the armored graphite 77.

The main-reflection plate 73 and the sub-reflection plate 74 reflect far infrared rays, and an aluminum plate having an excellent reflective power is commonly used as the main-reflection plate 73 and the sub-reflection plate 74. Alternatively, the main-reflection plate 73 and the sub-reflection plate 74 can be manufactured by applying far infrared radiating materials 73b and 74b to metal plates 73a and 74a, respectively, as shown in FIGS. 7b and 7c. Preferably, the far infrared radiating materials 73b and 74b are made of aluminum.

The far infrared radiating material can also be coated, not only onto the funnel 76, but also, for example, onto the panel 78 or other component parts such as a shadow mask.

According to the display device of the present embodiment in FIG. 7a, far infrared rays are emitted from the surface of the funnel 76 of the CRT 72, some of them being emitted directly toward the front side of the CRT 72 and some far infrared rays radiated to the rear side of the CRT 72 being reflected by the main-reflection plate 73 and the sub-reflection plate 74 toward the front of the CRT 72.

In particular, the sub-reflection plate 74 simultaneously blocks and absorbs electromagnetic waves emitted from the deflection yoke 75 of the CRT 72.

Figure 8:
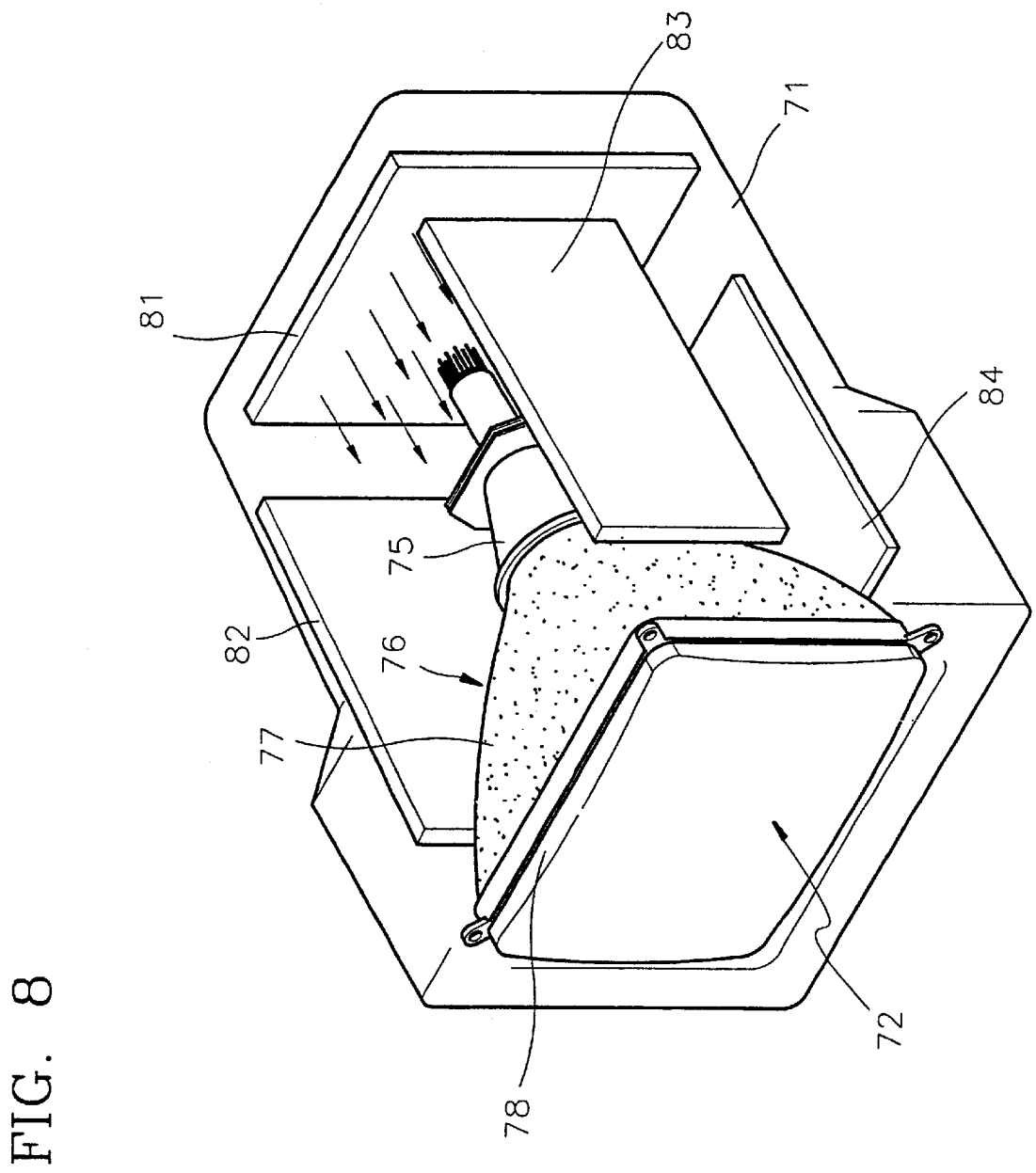
FIG. 8 is a partially cut away perspective view illustrating a display device according to a sixth embodiment of the present invention.

As shown in FIG. 8, the reflection plate can be installed to the rear, right, and left of a CRT. In FIG. 8, the same reference numerals of those of FIG. 7 denote the same members.

As described above, the armored graphite 77 coats the outer surface of the funnel 76 of the CRT 72 installed inside the main body case 71 of a display device, and a far infrared radiating material is mixed in the armored graphite 77.

The display device according to the present embodiment in FIG. 8 further includes a first reflection plate 81 installed to the rear of the CRT 72, second and third reflection plates 82 and 83 installed to the right and left thereof, and a fourth reflection plate 84 installed below the CRT 72. The structures of the first through fourth reflection plates 81, 82, 83 and 84 are the same as that of the reflection plate of FIG. 7.

According to the display device of the present embodiment in FIG. 8, far infrared rays radiated from the far infrared radiating material included in the armored graphite 77 of the CRT 72 are reflected by the first through fourth reflection plates 81, 82, 83 and 84 and emitted toward the front of the CRT 72. Hence, the radiation effectiveness of far infrared rays can be maximized.

The following experiment gives a more accurate understanding of the effectiveness of the far infrared generating apparatus according to the present invention and the display device adopting the same.

EXPERIMENTAL EXAMPLE

The effectiveness of the present invention will now be described on the basis of the results of an experiment made on a human body by a Japanese Tokyo Denki University.

When a person uses a computer, for a long period of time, having a monitor in which a CRT is installed, he or she feels fatigued in his or her whole body including eyes and shoulders, and considerably fatigued in his or her brain.

In the experiment, a person sequentially executed the following actions: (1) closing his or her eyes and relaxing for about 2 minutes; (2) performing word processing for about 5 minutes; (3) again being at ease with his or her eyes closed for about 2 minutes; (4) playing computer games for about 5 minutes; (5) again relaxing with his or her eyes closed for about 2 minutes; (6) drawing a picture for about 5 minutes; and (7) again relaxing with his or her eyes closed for about 2 minutes. Each of the above actions are performed in front of a computer adopting a conventional monitor and a computer adopting the monitor according to the present invention shown in FIG. 4. After the respective actions, a topography with respect to brain wave data upon resting with eyes closed is interpreted, and the degree of relaxation is found from the interpreted topography.

The brainwave measurement is a method of attaching many electrodes on the brain of a person, measuring electrical signals, and analyzing brain signals. Here, the measured signal is generally output as a complex waveform and classified as $\alpha$ waves, $\beta$ waves, $\theta$ waves, and $\delta$ waves. Thereafter, the intensity of the waves is displayed with different colors in a graph. This graph is commonly called a brain topography.

After computer work using the monitor according to the present invention, the user's brain wave is detected and compared to that of a person using a general monitor. As a result of the comparison, many $\alpha$ brain waves are generated in the case of the monitor according to the present invention. That is, it is known that a person working in front of the monitor according to the present invention is more comfortable and peaceful than a person working in front of the general monitor.

The above-described theoretical basis is, as described above, that an α wave, which is important to interpret the relaxation experiment, among α, β, θ, and δ waves divided from the brain waves according to frequency characteristics, is a brain wave having a frequency of 8 to 13 Hz and output from a human brain in a deep relaxed state. The relaxation state of a person in the experiment is interpreted using the brain topography obtained by pseudo coloring potential levels on the basis of such a principle.

After each action, a change in heart rate upon relaxing with eyes closed, and a heart beat R point potential are measured, a heart beat R—R interval quake is Fourier-interpreted, and the reaction of the autonomic nervous system was investigated from a heart beat spectrum.

In the R point potential change data of a heart rate and an electro cardiogram (ECG), an increase in heart rate represents that the sympathetic nervous system holds priority to the autonomic nervous system. If a heart beat spectrum is obtained by Fourier-interpreting the quake of the ECG at R—R intervals, the superiority between the sympathetic nervous system and the parasympathetic nervous system can be determined.

The time Δt of heart beat R—R interval is irregular, and it is known that the quake is determined according to the antagonism of the sympathetic and parasympathetic nervous systems in the autonomic nervous system. In Fourier transformation, data at equally-spaced time intervals can be transformed into frequency data. However, even when the time Δt is irregular, fast Fourier transformation (FFT) is possible since the data at irregular time intervals can be transformed to data of regular intervals.

Figure 9:
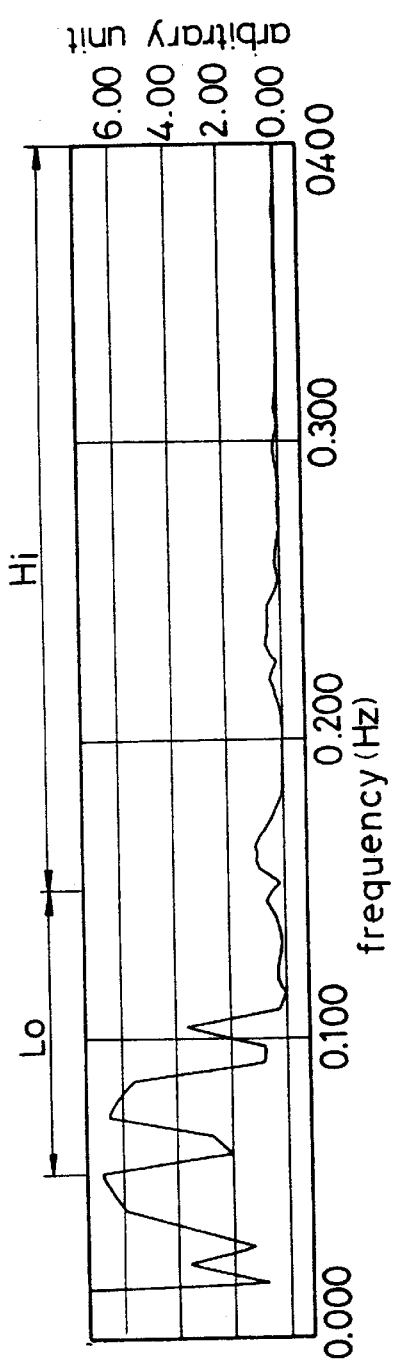
FIGS. 9 and 10 are graphs showing the results of experiments performed on a conventional display device and a display device according to the present invention.
Figure 10:
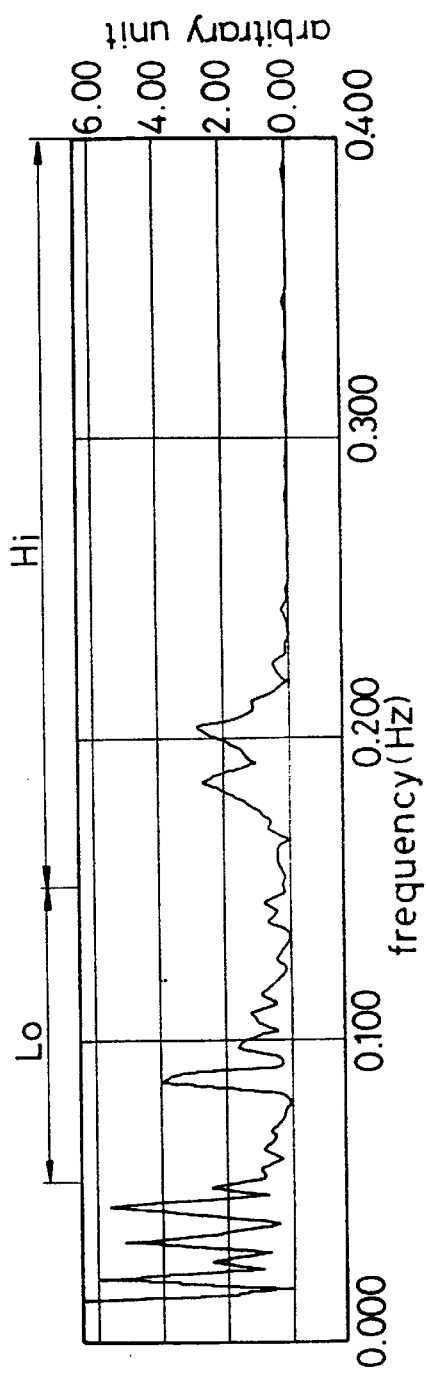

Data of the fast fourier transformation is shown in the graphs of FIGS. 9 and 10. Here, FIG. 9 is a graph for a conventional monitor, and FIG. 10 is a graph for a monitor provided with a far infrared ray generating device according to the present invention.

Referring to the graphs, several peaks exist in a frequency range between 0.05 Hz and 0.4 Hz. A peak appearing between 0.05 Hz and 0.15 Hz, among the several peaks, relates to the activity of the sympathetic nervous system in the autonomic nervous system. That is, this peak is a region (Lo) where a sympathetic nerve is dominant. A peak appearing between 0.150 Hz and 0.4 Hz is a region (Hi) where a parasympathetic nerve is dominant, relating to the activity of the parasympathetic nervous system.

In the present invention, 0.15 Hz is set as a boundary for dividing the sympathetic and parasympathetic nerves after fast Fourier transforming the R—R interval of the heart rate, which is based on the following thesis: Perini, R. et al (1990) "The influence of exercise intensity on the power spectrum of heart rate variability". Eur. J. Appli. Physiol. 61:143–148.

It is known that the sympathetic nervous system holds priority in the day time when a human body is vigorous, and that the parasympathetic nervous system holds priority in the night time when a human body is relaxed. However, it is known that when the human body is relaxed even in the day time, the parasympathetic nerve holds priority and the action of the sympathetic nerve is degraded. That is, when a load is applied to a human, the activity of the sympathetic nervous system holds priority due to the load in the day time, thus causing a reverse operation to laxity. Thus, with a low frequency component of 0.05 to 0.15 Hz indicated by Lo and a high frequency component of 0.15 to 0.4 Hz indicated by Hi, when a single spectrum exists in each region, the state of antagonism of the two nervous systems can be investigated by calculating the ratio of V×Lo/V×Hi from the peak value V.

However, not only one peak of a spectrum exists in each frequency range, so when several peaks exist, the antagonism of the two nervous systems is investigated by calculating the area ratio of each region. This experiment also used this method. Accordingly, the state of the antagonism of the two nervous systems can be found out by calculating the ratio of (V×Lo/V×Hi).

In the present experiment, the first and last rest states with eyes closed with respect to each monitor can be expressed by the following Equation:

$$X = \text{area Lo} / \text{area Hi}.$$

When an X value with respect to the conventional monitor is standardized as 1, an X value with respect to the monitor according to the present invention is expressed by 0.36. Such a figure represents that the action of the sympathetic nervous system (Lo) decreases and the action of the parasympathetic nervous system (Hi) increases. Therefore, it can be recognized that the monitor according to the present invention makes a user feel less tired compared to the conventional monitor.

In the monitor according to the present invention, the X value is 0.36, which is smaller than the X value of 1 in the case of the conventional monitor. This figure means that the action of the sympathetic system does not increases again even when a subsequent activity is performed, and the effect of relaxation is sustained long.

In FIG. 10 showing the results of a FFT on the ECG R—R interval of a person using a monitor which is a display system according to an embodiment of the present invention, the region (Hi) where the parasympathetic nervous system is dominant is relatively wider than the region Lo, which represents that the person is relaxed.

Also, when a far infrared radiating material is provided in the display device as shown in FIG. 5, adjustment of room humidity is also possible. Since the crystal structure of the far infrared radiating material has many pores, adjustment of the room humidity is understood as being made by the pores absorbing and releasing moisture.

The far infrared radiating material also has an excellent deodorizing function since it has a specific surface area of about 35 to 48 which is measured by a Brunauer Emmetto Teller (BET) measuring method, being a method of measuring the specific surface area of a material.

In order to ascertain the effectiveness of the far infrared ray reflection plate, a thermography test on the display device including the reflection plate of FIG. 8 and a conventional display device was executed. The thermography test was performed with a model TH3100 from NEC San-ei Instruments, Ltd in Japan being a thermograph capable of measuring a far infrared ray having a wavelength band of 8 to 13 μm. The thermograph represents data as a picture, and the radiation intensities of far infrared rays are distinguished by a change in the color of the picture. The radiant intensities are output as real values or absolute values. The results of a thermography test for 2 hours and 43 minutes after each of the display devices operates are shown in the following Table.

|  | maximum temperature of front surface (screen surface) | maximum temperature of rear surface |
| --- | --- | --- |
| display system according to the present invention | 32.9 ° C. | 29.0 ° C. |
| conventional display system | 28.0 ° C. | 26.3 ° C. |

In the above Table, the maximum temperatures of front and rear surfaces denotes the maximum temperatures of the front and rear surfaces of a display device. According to the above results, it can be found out that the display device according to the present invention emits many far infrared rays.

According to the present invention, many far infrared rays are emitted toward the front of a display device, so that a beneficial effect is had on a human body. In particular, the far infrared rays are modulated at a specific frequency profitable for the human body by a modulating means while being emitted, thus improving an effect of relaxing the human body.

What is claimed is:

1. A far infrared ray generating apparatus comprising:
a case having an aperture in a front side;
a far infrared radiating material on an inside surface of the case for radiating far infrared rays; and
modulating means in the case for modulating the far infrared rays radiated from the far infrared radiating material at a modulation frequency.

2. The far infrared ray generating apparatus as claimed in claim 1, wherein the modulating means comprises at least two modulating means, each modulating means including a driving unit and a fan rotated by the driving unit, the fans of the modulating means being driven at different speeds to modulate the far infrared rays at frequencies of 0 to 10 Hz.

3. The far infrared ray generating apparatus as claimed in claim 2, wherein the driving unit is selected from the group consisting of a stepping motor, a solenoid, and an electromagnetic driving device.

4. The far infrared ray generating apparatus as claimed in claim 2, wherein one of the fans is driven to modulate the far infrared rays at a frequency of 0 to 2 Hz, and another of the fans is driven to modulate the far infrared rays at a frequency of 0 to 10 Hz.

5. The far infrared ray generating apparatus as claimed in claim 1, wherein the modulating means comprises:
a hinged member rotatably mounted inside a passage in the case for opening and closing the passage; and
a driving unit for rotating the hinged member.

6. The far infrared ray generating apparatus as claimed in claim 5, wherein the driving unit includes a stepping motor.

7. The far infrared ray generating apparatus as claimed in claim 5, further comprising an emission fan in the rear side of the case for emitting far infrared rays radiated from a far infrared radiating material through the aperture.

8. The far infrared ray generating apparatus as claimed in claim 5, including grilles in the aperture to control emitted far infrared rays.

9. A display device comprising:
a main body case having an aperture in a front side;
a cathode ray tube in the main body case;
a far infrared radiating material on at least one side surface of and inside the main body case; and
modulating means for modulating far infrared rays radiated from the far infrared radiating material and emitted through the aperture at a frequency.

10. The display device as claimed in claim 9, wherein the far infrared radiating material is located on an outer circumferential surface of a funnel of the cathode ray tube.

11. The display device as claimed in claim 10, wherein the modulating means comprises at least two modulating means, each modulating means including a driving unit and a fan rotated by the driving unit, the fans of the modulating means being driven at different speeds to modulate the far infrared rays at frequencies of 0 to 10 Hz.

12. The display device as claimed in claim 11, wherein one of the fans is driven to modulate the far infrared rays at a frequency of 0 to 2 Hz, and another of the fans is driven to modulate the far infrared rays at a frequency of 0 to 10 Hz.

13. The display device as claimed in claim 10, wherein the far infrared radiating material coated on the outer circumferential surface of a funnel of the cathode ray tube is mixed with an armored graphite.

14. The display device as claimed in claim 10, wherein the modulating means comprises:
a hinged member rotatably mounted in the aperture for opening and closing the aperture; and
a driving unit for rotating the hinged member.

15. The display device as claimed in claim 14, further comprising an emission fan for emitting far infrared rays radiated from the far infrared radiating material through the aperture.

16. A display device comprising:
a main body case having a first aperture in a front side;
a cathode ray tube in the main body case; and
a far infrared ray generator including
a case having a second aperture in a front surface of the case, aligned with the first aperture,
a far infrared radiating material on an inside surface of the main body case for radiating far infrared rays, and
modulating means in the main body case for modulating far infrared rays radiated from the far infrared radiating material at a frequency.

17. The display device as claimed in claim 16, wherein the modulating means comprises:
a hinged member rotatably mounted in a passage in the case for opening and closing the passage; and
a driving unit for rotating the hinged member.

18. The display device as claimed in claim 16, further comprising an emission fan mounted in the rear side of a case for emitting far infrared rays radiated from the far infrared radiating material through the first and second apertures.

19. A display device comprising:
a main body case;
a cathode ray tube inside the main body case; and
at least one far infrared ray emission plate inside the main body case, the far infrared ray emission plate comprising a plate and a coating of a far infrared radiating material on the plate.

20. The display device as claimed in claim 19, wherein the far infrared radiating plate is located on a rear side of the cathode ray tube.

* * * * *